United States Patent [19]

Flower

[11] Patent Number: 5,279,298
[45] Date of Patent: Jan. 18, 1994

[54] METHOD AND APPARATUS TO IDENTIFY AND TREAT NEOVASCULAR MEMBRANES IN THE EYE

[75] Inventor: Robert W. Flower, Hunt Valley, Md.

[73] Assignee: The Johns Hopkins University, Baltimore, Md.

[21] Appl. No.: 979,691

[22] Filed: Nov. 20, 1992

[51] Int. Cl.$^5$ .............................................. A61B 3/12
[52] U.S. Cl. ................................... 128/633; 128/664; 351/206; 351/221; 606/4
[58] Field of Search ............... 128/633–4, 637, 644.7, 653.4, 654, 745; 606/2, 3, 4; 356/39–41; 351/206, 213–214, 205, 212, 211, 221; 607/89

[56] References Cited

U.S. PATENT DOCUMENTS

| | | |
|---|---|---|
| 3,893,447 | 7/1975 | Hochheimer et al. |
| 4,412,543 | 11/1983 | Vassiliadis et al. ................. 128/633 |
| 4,573,778 | 3/1986 | Shapiro ........................... 128/633 X |
| 4,608,990 | 9/1986 | Elings ................................ 128/633 |
| 4,786,813 | 11/1988 | Svanberg et al. ............... 128/633 X |
| 4,799,783 | 1/1989 | Takahashi et al. |
| 4,821,117 | 4/1989 | Sekiguchi ........................ 128/665 X |
| 4,842,401 | 6/1989 | Maurice ............................ 128/633 |
| 5,092,331 | 3/1992 | Nakamura et al. .................. 128/634 |
| 5,141,303 | 8/1992 | Yamamoto et al. ................. 351/211 |
| 5,163,437 | 11/1992 | Fujii et al. ......................... 128/665 |

FOREIGN PATENT DOCUMENTS

DE 3926652 4/1991 Fed. Rep. of Germany.

OTHER PUBLICATIONS

R. W. Flower and G. J. Klein, Pulsatile Flow in the Choroidal Circulation: A Preliminary Investigation, 1990 4, pp. 310–318, EYE.
G. J. Klein, R. H. Baumgartner and R. W. Flower, An Image Processing Approach to Characterizing Choroidal Blood Flow, Apr. 4, 1990, pp. 629–637, Investigative Ophthalmology & Visual Science, vol. 31, No. 4.

Primary Examiner—Angela D. Sykes
Attorney, Agent, or Firm—Mary Louise Beall

[57] ABSTRACT

The method and apparatus of the invention allow a neovascular membrane in the ocular vasculature of the fundus of the eye to be identified and treated while minimizing damage to the sensory retina. First a bolus of fluorescent dye is injected and allowed to circulate through the ocular vasculature. When the fundus is diffusely irradiated with laser energy, dye present in the vasculature fluoresces. A neovascular membrane is identified when a particular area of fluorescence differs from the fluorescence of the surrounding normal vasculature. To treat the neovascular membrane, a second laser is focused on the site of the membrane and a second bolus of fluorescent dye is injected. When the presence of the second injection of dye is detected, energy from the focused laser is applied to damage or destroy the neovascular membrane.

26 Claims, 3 Drawing Sheets

METHOD AND APPARATUS TO IDENTIFY AND TREAT NEOVASCULAR MEMBRANES IN THE EYE

BACKGROUND OF THE INVENTION

This invention is a method and apparatus to detect and treat neovascular membranes in the ocular vasculature of the fundus of the eye. It is related to U.S. Pat. No. 3,893,447 to Bernard F. Hochheimer and the present inventor and entitled "Simultaneous Angiography of the Separate Retinal and Choroidal Circulations". According to this patent, simultaneous angiography of the separate retinal and choroidal circulations of the human eye is accomplished following a single intravenous injection of a mixture of at least two dyes having differing spectral characteristics. In a preferred embodiment of the patent, a single injection of a mixture of sodium fluorescein and indocyanine green dyes is administered intravenously to the subject. Angiograms of the separate retinal and choroidal circulations are then taken simultaneously with a fundus camera modified to separate the electromagnetic radiation emanating from the eye which is respectively attributable to the sodium fluorescein dye and to the indocyanine green dye.

This patent also disclosed a fundus camera system similar to that used in the present invention.

A scientific article entitled "An Image Processing Approach to Characterizing Choroidal Blood Flow", *Investigative Ophthalmology & Visual Science*, Vol. 31, No. 4, April, 1990 by G. J. Klein, R. H. Baumgartner and R. W. Flower, the present inventor, discusses the use of indocyanine green (ICG) dye angiography in the study of choroidal blood flow in the human eye using angiographic image processing algorithms.

A second scientific article entitled "Pulsatile Flow in the Choroidal Circulation: A Preliminary Investigation" *Eye*, (1990) 4, 310-318 by R. W. Flower and G. J. Klein, also discusses the computer aided image analysis of ICG choroidal angiography.

U.S. Pat. No. 3,926,652 relates to ophthalmic equipment for angiographic examination of the eye.

U.S. Pat. No. 4,799,783 discloses a fundus camera for performing fluorescein angiography of the eye. It incorporates a barrier filter seated in the imaging optical path and an exciter positioned in the illuminating optical path.

OBJECTS OF THE INVENTION

A first object of the invention is a method to identify, locate and treat neovascular membranes in the ocular vasculature of the fundus of the eye.

Another object of the invention is the apparatus used to practice the method of identifying, locating and treating the neovascular membranes.

An object of the invention is an improved fundus camera including a first source of light energy to assist in the identification of neovascular membranes and a second source of light energy to treat the neovascular membranes.

Another object of the invention is to determine the precise instant at which the maximum concentration of intravenously injected dye arrives at the neovascular membrane to be treated.

Still another object of the invention is the selection and the amount of the fluorescent dye composition to be injected intravenously to identify and then to damage or destroy the neovascular membrane when the dye composition is excited through the application of light energy.

SUMMARY OF THE INVENTION

Associated with a number of pathological conditions is the growth of ocular neovascular membranes. These membranes are often in close proximity to the sensory retina of the eye. If the abnormality arises from the retinal vessels, it is called a retinal neovascularization. If it is from the choroidal vessels, it is called a choroidal neovascularization (CNV). Both kinds of neovascularizations can diminish vision: in the case of retinal neovascularization by blocking light focused by the eye's lens into the retina, and in the case of CNV by distorting the ordinarily flat sensing retina. CNV is particularly difficult to identify and treat, especially when it lies beneath the retinal pigment epithelium or RPE, a layer of pigmented cells between the retina and the choroid since the RPE does not readily transmit visible light ordinarily used to examine the retina.

The method and apparatus of the invention allow neovascular membranes of the ocular vasculature of the fundus of the eye to be identified and treated by first injecting a bolus of fluorescent dye and diffusely irradiating the fundus with laser light of a wavelength maximally absorbed by the dye. As it circulates, dye present in the vasculature fluoresces. A neovascular membrane is identified when a particular area of fluorescence differs from the fluorescence of the surrounding normal vasculature. The wavelength of light associated with the dye fluorescence and the irradiating laser are chosen to overcome the optical barriers imposed by the ocular tissues, especially the RPE.

In addition to identifying the neovascular membrane, while the dye bolus passes through the vasculature, information is obtained and recorded as to the location at which the dye first enters the fundus as well as the time thereafter ($\Delta t$) until the maximum dye concentration is present in the identified neovascular membrane.

To treat the neovascular membrane, light from a second laser is focused onto the site of the membrane, and a second bolus of fluorescent dye is injected. At $\Delta t$ after the entrance of the second bolus of dye into the fundus is detected, a burst of energy from the focused second laser is applied. The laser energy is applied at a sufficiently high level at the precise moment the maximum concentration of dye is present in the membrane. This damages or destroys the neovascular membrane while using the minimum necessary laser energy in the process.

The burst of laser energy is within the limits of the maximum flux density or irradiance which can be applied to the fundus of the eye and absorbed by the neovascular membrane within a particular time span without causing excessive damage to the normal tissues of the eye. It is understood that the longer the duration of exposure, the lower is the allowable level of irradiance. However the flux density of energy applied and the duration of the application depend on the type of dye or mixture of dyes used.

The type of dye and the wavelength of light emitted by the focused second laser need not be identical to those used with the first diffusely focused laser used to identify the neovascular membrane and to position and focus the second laser. However, it is advantageous to mix the second dye with a quantity of the first dye since the diffusely focused first laser is used following injection of the second dye bolus in order to determine when the second dye bolus first enters the eye.

The amount of dye injected is a "bolus" which in this case is defined as a discrete aliquot or measured dosage of the fluorescent dye. The objective is to have as intact a quantity of dye as possible arrive at the eye with minimum dilution in the blood in which it is flowing. This insures that the dye present in the vasculature is at sufficient concentration to maximally absorb light energy from the second laser source.

According to the invention, when the first bolus of fluorescent dye is injected intravenously into a patient, a fundus camera focuses an image of the fundus of the eye onto an image acquiring means, for example a video camera connected to the fundus camera. As the bolus of dye permeates the ocular vasculature, light energy from the first laser, diffusely focused onto the fundus by the fundus camera, causes the dye to fluoresce. The fundus camera, in conjunction with the image acquiring means and an image recording and analyzing means such as a computer, then records the passage of the dye through the ocular vasculature. This recording of the fluorescing dye present in the vasculature constitutes a map. On this map, abnormalities of the vasculature such as neovascular membranes differ from the normal vasculature in an observable way, for example, in shape, intensity of fluorescence or in the speed with which the dye moves through the abnormality. Based on this map and with the assistance of the fundus camera, the practitioner is able to focus the output of the second laser through the optics of the fundus camera directly onto the specific location of the abnormality, and treatment may be applied through the fundus camera by applying the necessary output of the second focused laser at the precise moment when the maximum concentration of a second bolus of dye arrives in the neovascularization. A characteristic of the second bolus of dye is that is preferentially absorbs the wavelength of light emitted by the focused laser.

The word "treatment" as used here means to destroy or damage the vascular abnormality so that it is essentially removed from the ocular vasculature or reduced significant in size. Treatment of the identified vasculature abnormality requires a second bolus of dye to be administered intravenously. The type of dye in the second bolus is specifically chosen to include at least one composition which, when excited by the laser light energy, damages or destroys the abnormality.

DESCRIPTION OF THE PREFERRED EMBODIMENTS

The invention is a method and apparatus to detect and treat abnormalities such as neovascular membranes in the ocular vasculature of the fundus of the eye while doing minimal damage to the sensory retinal tissue. In order to understand the invention, various structures of the eye must be defined.

Figure 1:
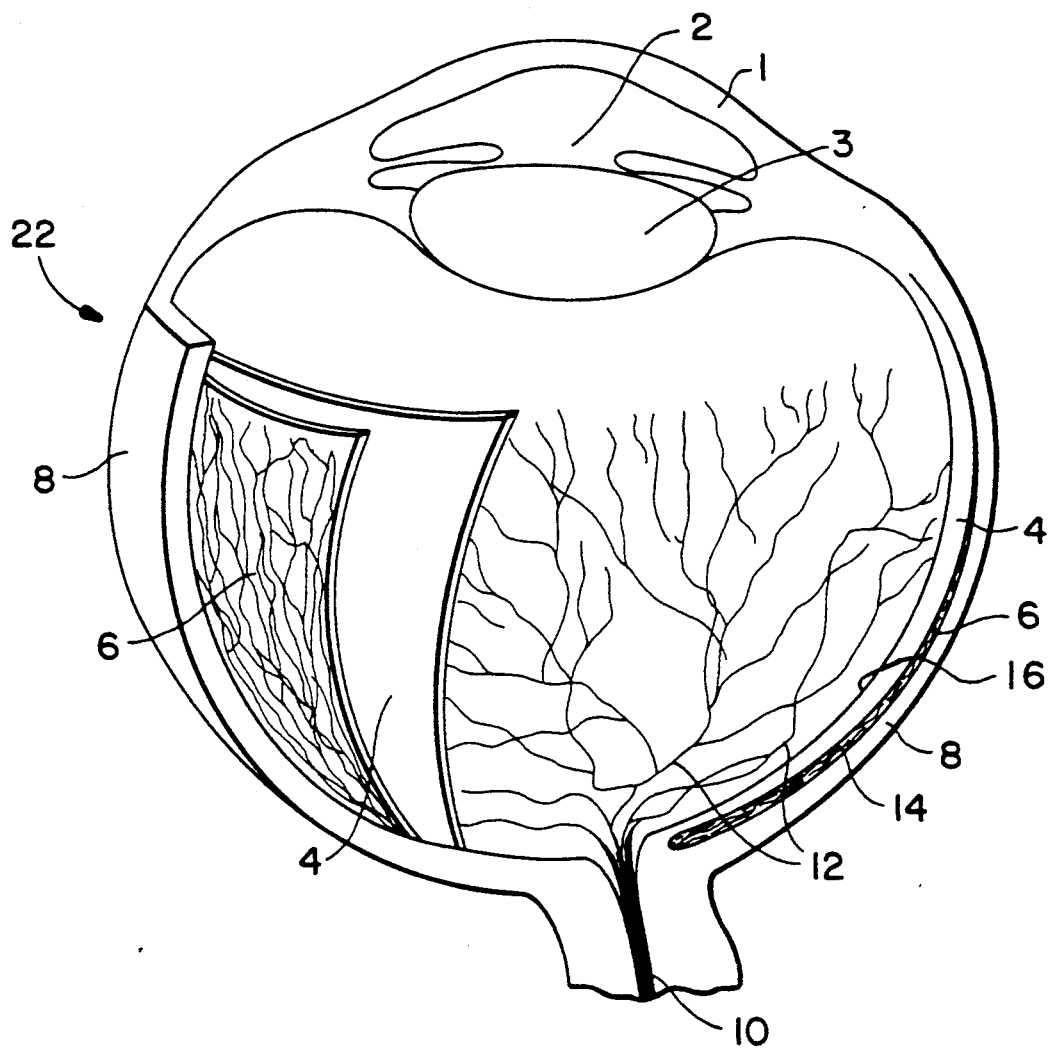
FIG. 1 is a sectional view of the eye showing its various components and vasculature.

As shown in FIG. 1, the eye is a sphere 22 whose outside surface is generally defined by the cornea 1 at the front of the sphere and the sclera 8 covering the rest of the sphere. Located behind cornea 1 is the pupil 2 and the lens 3. Within the back of the sphere are several layers including the sclera 8, the choroid 6 and the retina 4. The pigment epithelium 14 is a thin layer between choroid 6 and retina 4. Also at the back of the eye are the central retinal artery and vein 10. The inside of the back of the sphere is called the fundus, generally indicated by 16.

The ocular vasculature is the general name for blood vessels found in the eye. This includes the choroid 6, a highly vascular layer of the eye, and the retina 4, containing the retinal arterioles and veins 12.

A neovascular membrane can be defined as an abnormal growth in blood vessels of the eye and typically arises from choroid 6 or retina 4. Photoreceptors (not shown) are located within the sensory retina adjacent to retinal pigment epithelium 14. Retina 4 is transparent, and when abnormalities occur in the retinal arterioles and veins 12, light is prevented from reaching the underlying photoreceptors and vision is disturbed. This type of retinal abnormality is often a swollen blood vessel or several blood vessels clumped together. Since blood is not very transparent to visible light, this abnormality interferes with normal vision; it is often associated with diabetes.

Abnormalities in choroid 6 can also affect vision. For example, blood vessels from choroid 6 can break through pigment epithelium 14 and cause it to balloon. This effect is similar to a bubble in a glass and causes visual distortion by displacing the retina from its normal position, flat against the choroidal surface.

The process of the invention allows these neovascular membranes to be treated selectively while not significantly affecting the surrounding eye tissues.

Figure 2:
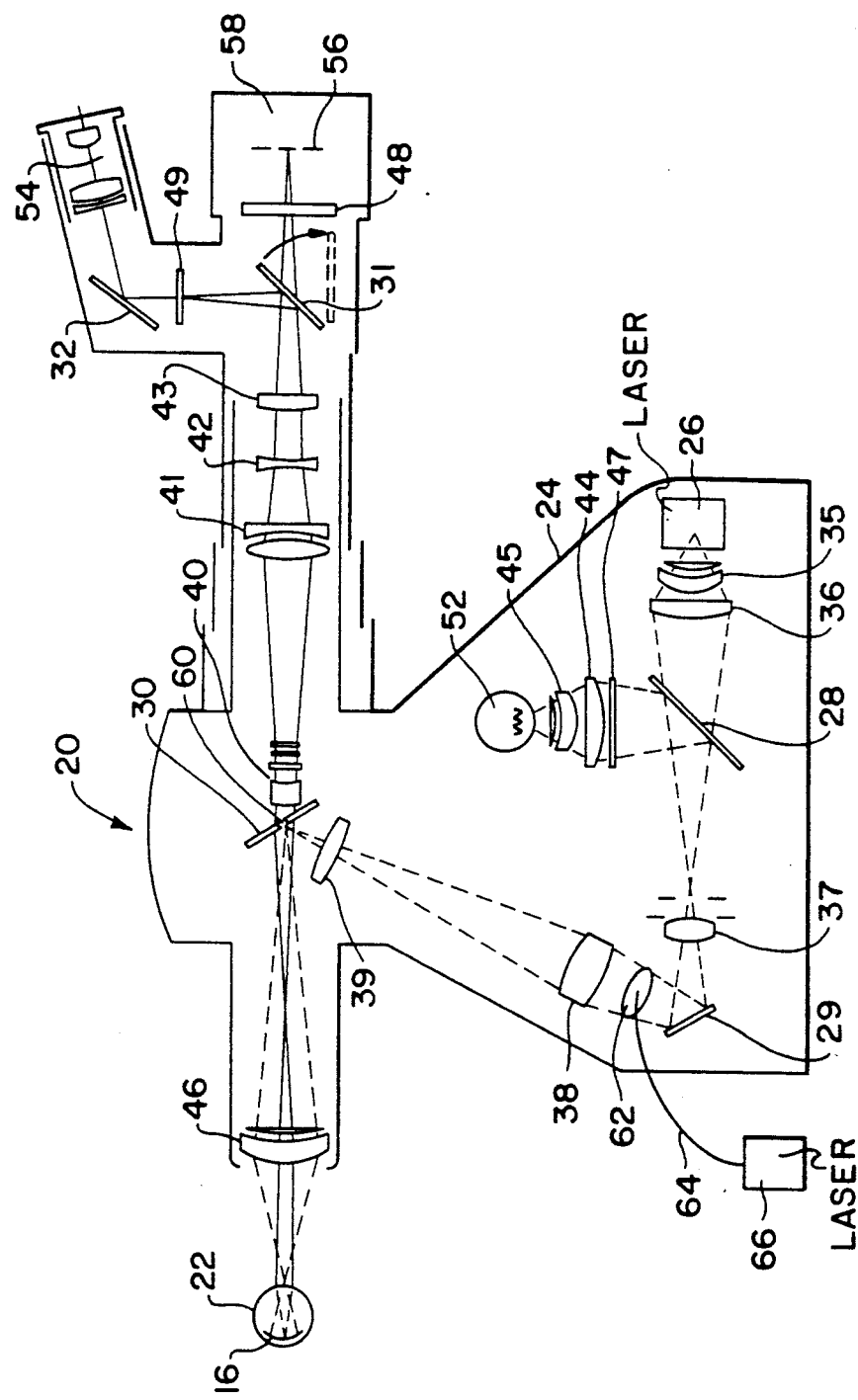
FIG. 2 is a schematic diagram of the fundus camera of the invention.

The fundus camera of the invention is part of the apparatus used to practice the process of the invention and will be described referring to FIG. 2 wherein the camera is generally shown at 20. Camera 20 focuses on the fundus 16 of the sphere of the eye 22 (see FIG. 1). Housing 24 of camera 20 encloses a variety of optical elements including a first laser 26; mirrors 28, 29, 30, 31 and 32; lenses 35, 36, 37, 38, 39, 40, 41, 42, 43, 44, 45, and 46; filters 47, 48 and 49; a white light source 52; eyepiece assembly 54 and the light sensitive face 56 of the image acquiring means 58. Mirror 30 has a hole 60 at its center. Between mirror 29 and lens 38 is located a transparent support 62 for fiber optic 64 connected to a second laser 66. The lenses, filters and mirrors form an adjustable system for focusing light on the fundus.

The fundus may be observed directly by the practitioner through eyepiece assembly 54 with light provided by white light source 52. The white light, focused by means of lens 44 and 45, passes through filter 47, and is reflected by appropriately tilted hinged mirror 28 through lens 37 to mirror 29. Mirror 29 reflects the light through transparent support 62 and lenses 38 and 39 to mirror 30 where it is reflected through lenses 46 into eye 22 and is focused on fundus 16. The light, now transmitting the image of the fundus, returns through lenses 46 which direct the light through hole 60 in mirror 30 and through lenses 40, 41, 42 and 43 to hinged mirror 31 which is appropriately tilted to reflect the light through filter 49 to mirror 32 and into eyepiece 54. Thus, when the white light source 52 is on and mirrors 28 and 31 are appropriately tilted, the practitioner may visually and directly examine the fundus of the eye.

Laser energy is applied in a similar fashion but with tilting mirrors 28 and 31 removed from the path of the laser light. The first laser 26 supplied energy through lenses 35, 36 and 37 to mirror 29 where it is reflected through transparent support 62 and lenses 38 and 39 to mirror 30. Here it is reflected through lenses 46 and into eye 22 and is diffusely focussed on fundus 16 where it excites the fluorescent dye present (if any) in the vasculature, causing it to fluoresce. This fluorescence enters the fundus camera through lenses 46, hole 60 in mirror 30, through lenses 41, 42, 43 and 48 to the light sensitive face 56 of image acquiring means 58.

Energy from the second laser 66 is applied through flexible fiber optic 64 held by transparent support 62 and thereafter follows the same path to eye 22 as for first laser 26 described above. Second laser 66 is focused on the abnormality to be treated by means of transparent support 62 positioned in a plane conjugate with the plane of the fundus. Support 62 is provided at its center with a hole through which the end of fiber optic 64 is inserted; the other end of the fiber optic is connected to second laser 66. Using diffuse irradiation from first laser 26 or low level light from white light source 52 and viewing the fundus through eyepiece assembly 54, the practitioner moves transparent support 62 to focus the support end of fiber optic 64 on the fundus. This end appears as a darkened spot which may be moved around on the fundus by moving transparent support 62. In this fashion, second laser 66 is focused precisely on the abnormality by positioning the darkened dot on the abnormality. The energy from second laser 66 is thus applied only to the abnormality and causes little if any damage to the surrounding normal vasculature. In this particular embodiment, support 62 is moved using a joy stick type mechanism (not shown).

Figure 3:
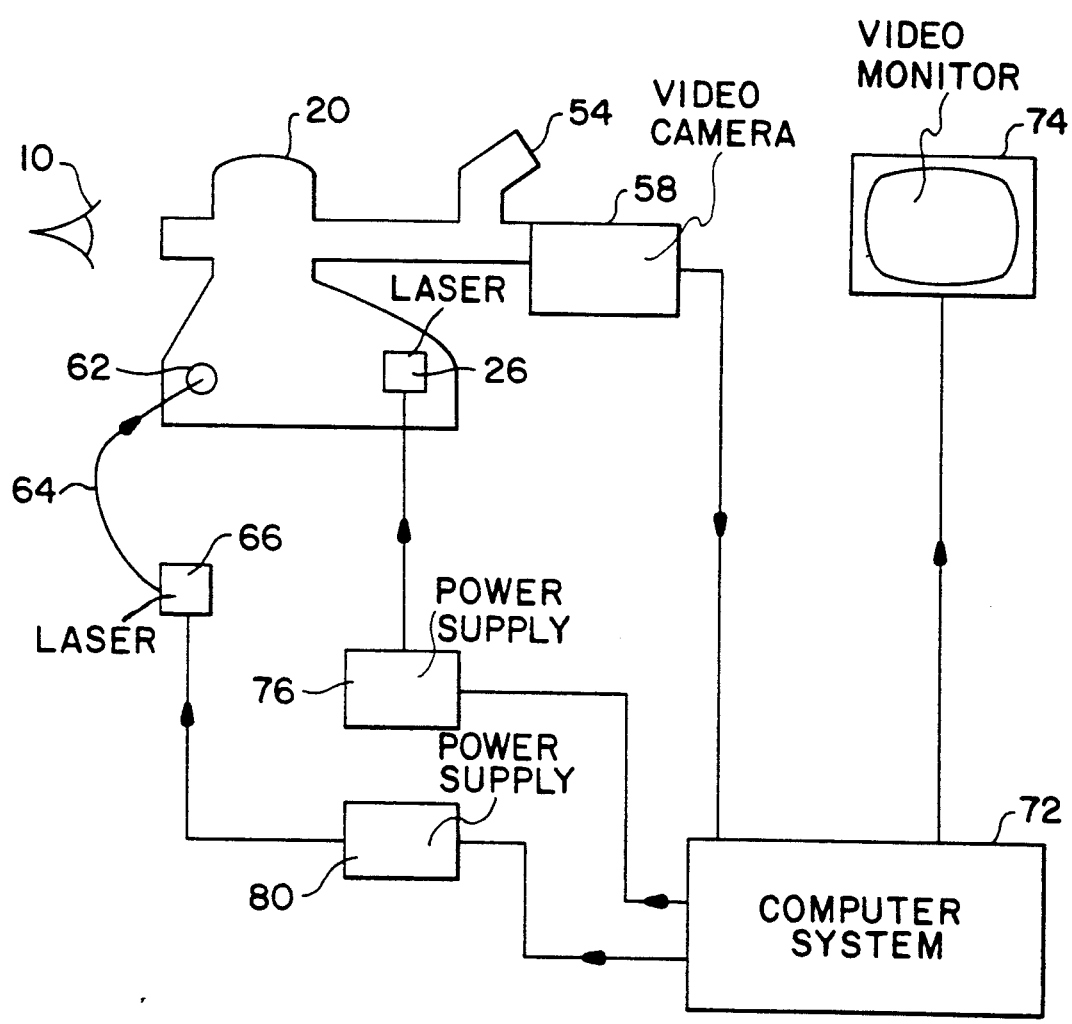
FIG. 3 is a block diagram of the apparatus of the invention.

The fundus camera 20 described is above is part of the apparatus of the present invention shown in FIG. 3. Fundus camera 20 provides images which are captured by the acquiring means 58, in this particular case a video camera. Acquiring means 58 is connected to analyzing and recording means 72, in this case a computer and its associated software (computer system). The computer records successive images or frames of the fundus of the eye with the passage of time. The individual frames are acquired and stored in computer system 72 by frame grabber components (not shown). Computer system 72 also sends the images to be displayed on video monitor 74 for viewing by the practitioner for diagnosis. First laser 26, fired by the practitioner using computer system 72 to operate first power supply 76, diffusely illuminates the fundus 16. Second laser 66 is fired by a timing device in computer system 72 through second power supply 80.

With the assistance of computer system 72, individual frames or images of the fundus are displayed on the video display or monitor 74. The practitioner is able to view each frame for diagnosis and treatment purposes. The computer system also comprises a keyboard (not shown) to be used by the practitioner to select the individual frames to be examined and to instruct the computer system to perform other tasks.

As described above, abnormalities of the vasculature differ from the normal vasculature of the fundus in an observable way. For example, as the fluorescent dye moves through the fundus, abnormal areas of the fundus can be identified through comparison with normal areas. For example, an abnormality may be detected when an area or location differs in shape, intensity or quality of fluorescence or the speed with which the dye moves through the area differs significantly from that of the normal fundus.

By viewing and analyzing the images recorded by computer system 72, the practitioner notes the location (A) of the first appearance of fluorescence in the fundus and the location (B) of the neovascular abnormality and the exact moment of maximum fluorescence at location (B) relative to its appearance at (A). The computer computes the exact time ($\Delta t$) between the appearance of fluorescence at location (A) and the maximum dye fluorescence at location (B). These are recorded in computer system 72. The maximum dye fluorescence indicates maximum dye concentration at location (B).

In the next step, the practitioner focuses second laser 66 directly on the detected abnormality at location (B) and instructs computer system 72 to begin operation. Then, the patient is given a second intravenous bolus injection containing fluorescent dye. When the dye arrives at the eye, the beginning of fluorescence is detected again at location (A) by computer system 72, and after waiting a time ($\Delta t$), computer system 72 causes second laser 66 to fire. The laser energy is then absorbed by the dye in the abnormality causing the abnormality to be damaged (i.e. reduced in size) or destroyed.

Because the output of laser 66 is tightly focused on location (B), the laser energy is applied only to location (B). Because the laser energy is applied at time ($\Delta t$), the dye concentration in the abnormality is at its maximum. This allows high power laser energy to be maximally absorbed by the dye with little, if any damage to the surrounding normal fundus. The result of this energy absorption is to produce either heat or a photochemical reaction which will destroy or coagulate the blood vessel containing the dye. Ideally, selection of the laser wavelength and the dye are such that the light is maximally absorbed by the dye and minimally by the retina and other ocular tissues.

In summary, to operate the process and apparatus of the invention, the patient is positioned in proximity to the apparatus so that the fundus camera 20 is able to focus on the fundus of the patient's eye 70. Using white light source 52 and eye piece assembly 54, the practitioner aligns the optical pathway of fundus camera 20 with the patient's eye 70 and diffusely focuses first laser 26 on the fundus. Computer system 72 is instructed to diffusely irradiate the fundus with light energy from first laser 26 and to begin acquiring, recording and analyzing images. The patient is given the first bolus of dye composition intravenously. The practitioner examines each acquired image on video monitor 74 and detects location (A) and location (B). The computer computes ($\Delta t$). Second laser 66 is focused on location (B) by moving transparent support 62 and by adjusting the focus of fundus camera 20 as required. Computer system 72 is again instructed to begin acquiring, recording and analyzing images and to detect the exact instant the second dye composition appears at location (A). The patient is given the second bolus of dye composition intravenously. When the entry of the dye into the fundus at location (A) is detected, computer system 72 waits for a time ($\Delta t$) and fires second laser 66. This destroys or damages the abnormality.

In this particular embodiment the dye in the first bolus is indocyanine green (ICG) but may be a mixture of ICG and sodium fluorescein as disclosed in U.S. Pat. No. 3,893,447, described above. The dye in the second bolus is also ICG but may be one or a mixture of ICG, rose bengal and any other dye which, when sufficiently excited by laser energy, destroys or damages the abnormality. Another useful dye is NK 1841, an analog of ICG. Note that rose bengal is a dye which, with proper excitation, produces oxygen radicals which in turn destroy the cell membranes of targeted abnormal blood vessels.

The first laser in this embodiment is a diode laser having a wavelength in the range of 805 nm and an intensity in the range of 35 mW-170 MW per cm² of retina. The second laser is also an 805 nm diode laser but may also, for example, be a diode laser with a wavelength principally absorbed by rose bengal dye. The applied intensity of the second laser is in the range of 50-200 mW for a 50 $\mu$ diameter spot on the retina.

In this embodiment, the fundus camera is a modified standard Zeiss fundus camera. The computer system comprises the following components: A Compaq Disk Pro 386/20e computer, Data Translation DT-2681 frame grabbers, Data Translation DT-7020 array processor and a Literal Corp. WCXOE Optical Storage System 525WC.

Variations of the preferred embodiment enhance the quality of the images obtained using the first laser. The quality of the image depends directly on the level of retinal irradiance employed to excite the dye to fluorescence as it passes through the ocular circulations. Use of low level laser illumination, on the order of 35 mW per cm², permits continuous retina exposure without damage. However, such a low level produces weak fluorescence signals which must be greatly amplified in order to form useful images of the vasculature. Moreover, the signal-to-noise ratio is not high, and amplification of these signals adds additional noise to the resultant image.

Better images having a higher signal-to-noise ratio can be produced with a higher level of retinal irradiance. But, as stated above, the standard for determining the maximum permissible retinal irradiance is: the longer the exposure time, the lower is the allowable level of retinal irradiance. The entire dye transit time through the ocular vasculature, i.e., from early filling of the arterial vessels to late draining of the venous vessels occurs in less than 5 seconds. The object is to use the maximum safe level of retinal irradiance for the minimum amount of time which results in the highest possible signal-to-noise ratio and thus the best quality images.

A second embodiment includes continuously irradiating the fundus with the first laser at approximately 35 mW per cm² of retina. When fluorescence is detected, the laser intensity is instantaneously stepped up to a maximum of 170 mW per cm² for 5 seconds and then reduced to 35 mW per cm². This allows high signal-to-noise image to be acquired during the dye transit.

In a third embodiment, the first laser is a diode laser having a wavelength in the near infrared spectral region and coupled to the fundus camera optics by way of an integrating sphere so as to produce a completely uniform field of illumination. The image acquiring means used record the fluorescence images is a silicone array device sensitive to wavelengths near 805 nm and capable of being electronically gated or shuttered (i.e., opened and closed) at a rate of at least 15 frames per second. The first laser is operated in a pulsed mode rather than the continuous mode of the preferred embodiment where the firing of the pulses will be exactly synchronized to the time intervals during which the electronically shuttered image acquiring means is receiving light arising from the fluorescent dye present in the vasculature.

Under computer control, the first laser is pulsed to emit very short duration pulses of light at a duty cycle of less than 50% such that the average retinal irradiance will be less than 35 mW per cm² of retina; in this mode of operation, no time limit must be set as to the duration of retinal irradiance. The dye is injected and real-time digitized images will be acquired and analyzed by the computer, through its associated software, to detect any change in the brightness of the image above a preselected threshold. Any change in brightness results from the first fluorescing dye entering the vasculature, signaling that the transit of dye is about to commence. When the change is detected, the computer instantaneously increases the output level of the laser to maximum level so that the average retinal irradiance during the 5 second interval is the maximum safe limit of retinal irradiance, in the range of 200 mW. At the end of the 5 second interval, the laser output is instantaneously reduced once again to the 35 mW level.

The invention described is not intended to be limited to the embodiments disclosed but includes modifications made within the true spirit and scope of the invention.

I claim:

1. A process for locating and treating an abnormality in the ocular vasculature of the fundus of the eye of a living body, said process comprising:
   a. injecting a first bolus of a fluorescent dye composition into the circulatory system of the living body;
   b. allowing the first bolus to circulate through the body and through the ocular vasculature of the fundus;
   c. detecting the presence of the first bolus of dye in the ocular vasculature by diffusely irradiating the fundus of the eye with light energy from a first laser thus causing dye present in the vasculature to fluoresce;
   d. detecting the presence and location of the abnormality in the vasculature by examining the fluorescence in the vasculature and identifying at least one location (B) wherein the fluorescence differs from the fluorescence of the surrounding normal vasculature;
   e. focusing light energy from a second laser on the location (B) of the detected abnormality;
   f. injecting a second bolus of a second fluorescent dye composition into the circulatory system;
   g. detecting the presence of the second bolus of dye in the ocular vasculature; and
   h. applying light energy from a second laser to treat the detected abnormality.

2. A process according to claim 1, wherein steps c. and d. occur simultaneously and further wherein step c. includes:
   detecting the precise instant the first bolus enters the fundus; and
   measuring a time thereafter ($\Delta t$) of maximum fluorescence at the location (B).

3. A process according to claim 2, wherein step g. includes detecting the precise instant the second bolus enters the fundus by diffusely irradiating the fundus of the eye with light energy from the first laser thus causing dye present in the vasculature to fluoresce.

4. A process according to claim 3, wherein step h. is performed at the time ($\Delta t$).

5. A process according to claim 3, wherein step d. includes:
   acquiring successive images of the fundus with the passage of time;
   recording each image; and
   analyzing each image to identify at least one location (B) wherein the fluorescence differs from the fluorescence of the surrounding normal fundus.

6. A process according to claim 5, wherein in step g., the precise instant the second bolus of dye enters the fundus is detected at a location (A).

7. A process according to claim 5, wherein in step c, the light energy from the first laser is pulsed and further wherein the acquiring of successive images is shuttered and coordinated with the pulsed laser so that the images are acquired only during the laser pulse.

8. A process according to claim 2, wherein detecting the precise instant the first bolus enters the fundus includes:
   acquiring successive images of the fundus with the passage of time;
   recording each image; and
   analyzing each image to identify an exact location (A) at which the dye first enters the fundus.

9. A process according to claim 8, wherein in step c, the light energy from the first laser is pulsed and further wherein the acquiring of successive images is shuttered and coordinated with the pulsed laser so that the images are acquired only during the laser pulse.

10. A process according to claim 1, wherein the first and second lasers are independently focused on the fundus through and by a fundus camera.

11. A process according to claim 10, wherein the second laser is focused on the abnormality by:
   positioning a transparent support in a light path of the fundus camera and in a plane conjugate with the plane of the fundus camera, said support being provided with an opening holding a first end of a fiber optic connected at an opposite end to the second laser;
   diffusely irradiating the fundus of the eye through the transparent support with the first laser so that the first end of the fiber optic appears as a darkened spot on the fundus; and
   moving the transparent support and thus moving the darkened spot to be positioned on the abnormality.

12. A process according to claim 1 including pulsing the light energy from the first laser in step c.

13. A process according to claim 1, wherein the first and second lasers are diode lasers having a wavelength of about 805 nm, said first laser operating at an intensity in the range of 35 mW–170 mW/cm$^2$ of retina, said second laser operating at an intensity in the range of 50 mW–200 mW in a 50 $\mu$ diameter spot on the retina, and the first and second fluorescent dye compositions are indocyanine dye compositions.

14. A process according to claim 13, wherein the second fluorescent dye composition also comprises rose bengal dye.

15. A process according to claim 13, wherein the first fluorescent dye composition also comprises sodium fluorescein.

16. A process according to claim 1, wherein the relationship between the first laser and the first fluorescent dye composition and the relationship between the second laser and the second fluorescent dye composition are such that the wavelength of the laser is maximally absorbed by the respective dye composition.

17. A process according to claim 1, wherein the fundus is diffusely irradiated with light energy from the first laser prior to step c. and further wherein the intensity of the light energy is increased instantaneously when the presence of the first fluorescent dye compositions first detected in the fundus.

18. A process for locating and treating an abnormality in the ocular vasculature of the fundus of the eye of a living body, said process comprising:
   a. continuously irradiating the fundus of the eye with low level laser irradiation in the range of 35 mW per cm$^2$ of retina;
   b. injecting a first bolus of a fluorescent dye composition into the circulatory system of a living body;
   c. allowing the first bolus to circulate through the body and through the ocular vasculature;
   d. detecting the precise instant the presence of the first bolus of dye enters the ocular vasculature by detecting the first appearance of fluorescence in the fundus;
   e. operating the laser in a pulsed mode and at a high level of laser irradiation greater than 35 mW per cm$^2$ of retina but less than 170 mW per cm$^2$;
   f. acquiring successive images of the fundus with the passage of time as the dye moves through the fundus, using shuttered means for acquiring, while coordinating the laser pulse with the means for acquiring so that the images are acquired only during the laser pulse;
   g. continuously irradiating the fundus as in step a;
   h. detecting the presence and location of the abnormality in the vasculature by examining the fluorescence in the images and identifying at least one location (B) wherein the fluorescence differs from the fluorescence of the surrounding normal vasculature;
   i. focusing light energy from a second laser on the location (B) of the detected abnormality;
   j. injecting a second bolus of a second fluorescent dye composition into the circulatory system;
   k. detecting the presence of the second bolus of dye in the ocular vasculature; and
   l. applying light energy from a second laser to treat the detected abnormality.

19. An apparatus for locating and treating an abnormality in the ocular vasculature of the fundus of the eye of a patient comprising:
   a fundus camera focused on the fundus of the eye of a patient;
   a first laser which diffusely irradiates the fundus and excites a first fluorescent dye composition in the ocular vasculature of the fundus, said dye composition provided by an intravenous injection of a first bolus to the patient;
   means for acquiring images of the fundus, said means for acquiring connected to the fundus camera;
   means for recording and analyzing the images to detect and locate the abnormality, said means for recording and analyzing connected to the image acquiring means; and
   a second laser focusing on the detected abnormality and applying treatment to the abnormality by exciting a second fluorescent dye composition present in the abnormality, said second dye composition provided by an intravenous injection of a second bolus to the patient;

wherein said first and second lasers are independently focused on the fundus by and fired through the fundus camera.

20. An apparatus according to claim 19, wherein the fundus camera also comprises means to focus the second laser on the abnormality, said means comprising a moveable transparent support provided with an opening holding a first end of a fiber optic connected at an opposite end to the second laser, said transparent support located in a light path within the fundus camera and also located in a plane conjugate with the plane of the fundus.

21. An apparatus according to claim 19, wherein the first and second lasers are diode lasers having a wavelength in the range of 805 nm and the first and second fluorescent dye compositions contain indocyanine green dye.

22. An apparatus according to claim 19, wherein the relationship between the first laser and the first fluorescent dye composition and the relationship between the second laser and the second fluorescent dye composition are such that the wavelength of the laser is maximally absorbed by the respective dye composition.

23. An apparatus according to claim 19, wherein the first laser is able to operate in the continuous mode and in the pulsed mode.

24. An apparatus according to claim 23, wherein the means for acquiring images is shuttered and able to coordinate with the laser operating in the pulsed mode so that images are acquired only during a laser pulse.

25. An apparatus according to claim 19, wherein the first and second lasers are diode lasers having a wavelength in the range of 805 nm and the first fluorescent dye composition is indocyanine green dye and the second fluorescent dye composition is indocyanine green dye and rose bengal dye.

26. An apparatus according to claim 19, wherein the first and second lasers are diode lasers having a wavelength in the range of 805 nm and the first fluorescent dye composition is indocyanine green dye and sodium fluorescein dye and the second fluorescent dye composition is indocyanine green dye.

* * * * *